US012702634B2

(12) United States Patent
Yousfi et al.

(10) Patent No.: US 12,702,634 B2
(45) **Date of Patent: *Aug. 11, 2026**

(54) COSMETIC COMPOSITION COMPRISING A PARTICULATE CELLULOSIC COMPOUND, HYDROPHOBIC SILICA AEROGEL PARTICLES, AND A SEMICRYSTALLINE POLYMER

(71) Applicant: L'OREAL, Paris (FR)

(72) Inventors: Naïma Yousfi, Chevilly Larue (FR); Carole Guiramand, Chevilly Larue (FR)

(73) Assignee: L'OREAL, Paris (FR)

( * ) Notice: Subject to any disclaimer, the term of this patent is extended or adjusted under 35 U.S.C. 154(b) by 229 days.

This patent is subject to a terminal disclaimer.

(21) Appl. No.: 18/722,647

(22) PCT Filed: Dec. 20, 2022

(86) PCT No.: PCT/EP2022/086883

§ 371 (c)(1),
(2) Date: Jun. 21, 2024

(87) PCT Pub. No.: WO2023/118067

PCT Pub. Date: Jun. 29, 2023

(65) Prior Publication Data

US 2025/0049691 A1 Feb. 13, 2025

(30) Foreign Application Priority Data

Dec. 21, 2021 (FR) ....................................... 2114063

(51) Int. Cl.

| | |
|---|---|
| ***A61K 8/81*** | (2006.01) |
| ***A61K 8/02*** | (2006.01) |
| ***A61K 8/58*** | (2006.01) |
| ***A61K 8/73*** | (2006.01) |
| ***A61Q 1/00*** | (2006.01) |

(52) U.S. Cl.

CPC ............ *A61K 8/8152* (2013.01); *A61K 8/025* (2013.01); *A61K 8/585* (2013.01); *A61K 8/731* (2013.01); *A61Q 1/00* (2013.01)

(58) Field of Classification Search

CPC ...... A61K 8/8152; A61K 8/025; A61K 8/585; A61K 8/731; A61Q 1/00

See application file for complete search history.

(56) References Cited

FOREIGN PATENT DOCUMENTS

| | | |
|---|---|---|
| FR | 2 986 428 A1 | 8/2013 |
| FR | 3 025 095 A1 | 3/2016 |
| FR | 3 061 004 A1 | 6/2018 |

OTHER PUBLICATIONS

Mintel, Sep. 2, 2020, "Foundation," XP055952595, Database Accession No. 8021363.

International Search Report and Written Opinion dated May 8, 2023 from related application No. PCT/EP2022/086883 filed Dec. 20, 2022; 8 pp.

*Primary Examiner* — Trevor Love

(74) *Attorney, Agent, or Firm* — Womble Bond Dickinson (US) LLP

(57) ABSTRACT

The present invention relates to a composition, especially cosmetic composition, in particular for caring for keratin materials, comprising: at least one particulate cellulosic compound; at least hydrophobic silica aerogel particles; and at least one semicrystalline polymer containing at least one alkyl acrylate chain. It also relates to a cosmetic process for caring for keratin materials comprising the application to the keratin materials of said composition.

13 Claims, No Drawings

COSMETIC COMPOSITION COMPRISING A PARTICULATE CELLULOSIC COMPOUND, HYDROPHOBIC SILICA AEROGEL PARTICLES, AND A SEMICRYSTALLINE POLYMER

The present invention is directed toward proposing for the field of the care and hygiene of keratin materials, especially the skin and/or the lips, and in particular the skin, a novel composition that is most particularly advantageous with regard to its technical performance and the sensations it affords the user during its application to said keratin materials, in particular to the skin.

The term "keratin materials" is understood in particular to mean the skin and/or the lips, and preferably the skin.

TECHNICAL FIELD

Cosmetic compositions are commonly employed for hiding and/or unifying skin relief imperfections such as pores, wrinkles and/or fine lines and/or scars. In this regard, numerous solid or fluid, anhydrous or non-anhydrous, formulations have been developed to date.

When these compositions are more particularly intended for fading out the visibility of the skin relief, the formulator uses therein diffusing fillers or else soft-focus fillers. However, the corresponding compositions that are currently available do not prove to be entirely satisfactory, especially in terms of soft-focus performance.

In order to obtain a satisfactory degree of soft focus, it is often necessary to introduce a large amount of soft-focus fillers into the composition. However, this amount of soft-focus fillers can result in a destabilization of said composition and can result in cosmetic properties not in accordance with user expectations, in particular the formation of pills during the application of the product and/or after drying and/or penetration of the product into the skin, or else a dry effect after application giving rise to an unpleasant sensation, or even discomfort, for the user.

These defects are totally unacceptable for the user, since the application is neither uniform nor pleasant given this pilling effect on application or during the removal of the product. In addition, it gives a "dirty" impression on the skin, and makes it hard to apply the product to the whole face or use it daily.

Furthermore, the formulation of environmentally friendly cosmetic products has become a major challenge for meeting new consumer expectations, in particular regarding natural and/or eco-friendly products, i.e. products whose design and development take into account their environmental impacts.

Just like any other, conventional, cosmetic composition, eco-friendly and/or natural cosmetic compositions must meet performance and use criteria (stability, applicability, harmlessness, etc.).

PRIOR ART

In order to overcome these problems and to afford comfortable care that has a soft-focus effect, alternative oily presentation forms are currently proposed on the cosmetic market.

However, these formulations have the drawbacks associated with the presence of large contents of fatty phase and of fillers in the composition, namely producing shiny skin and/or the sensation of greasy and/or tacky skin. Furthermore, they also exhibit stability problems.

In addition, such oily formulations cause sensations of heat on the skin. Thus, they are reserved for certain specific types of skin and are generally applied very locally to specific regions of the face.

The use of silicones, and in particular crosslinked silicones, is another alternative. The reason for this is that starting materials of this type can combine a matte effect and a soft-focus effect. However, they have the drawback of being characterized by a relatively uncomfortable warm and greasy feel, with a "mask" effect.

In addition, the international market is currently witnessing a trend directed towards compositions devoid of silicone compounds and of microplastic compounds, with consumers showing a preference for products that can be used without risk that are also environmentally friendly.

It thus remains difficult for a person skilled in the art to develop compositions meeting these demands and which are homogeneous, stable and capable of affording an immediate visual result on the skin with a sensation of lightness and comfort on application, with a non-tacky deposit, this expected immediate result preferentially being good covering of imperfections in the uniformity of the complexion and/or relief imperfections.

DISCLOSURE OF THE INVENTION

There thus remains a need for cosmetic compositions that comply with current regulations and are stable and environmentally friendly, and which make it possible to mask skin imperfections while having good cosmetic properties, in particular in terms of optical and sensory effects, without exhibiting a pilling phenomenon nor a dry effect after application.

There also remains a need for novel formulations containing essentially products that are not subjected to criticism and that remain stable and homogeneous over time and under the effects of light and temperature.

There is also a need for such cosmetic compositions which are compatible with consumers' requirements, notably regarding the environment.

The present invention is specifically directed towards meeting these needs.

SUMMARY OF THE INVENTION

Thus, according to a first aspect, the present invention relates to a composition, especially cosmetic composition, in particular for caring for keratin materials, comprising:

- at least one particulate cellulosic compound;
- at least hydrophobic silica aerogel particles; and
- at least one semicrystalline polymer containing at least one alkyl acrylate chain.

Against all expectations, the inventors have found that the combination of the specific compounds as defined above makes it possible to improve the optical and sensory performance of a composition, and to obtain compositions that are stable and have a consistency suitable for the targeted cosmetic applications.

As will emerge from the examples below, the compositions according to the invention exhibit good soft-focus optical effects, are stable and do not exhibit the problem of pilling.

The compositions according to the invention make it possible to combine optical and sensory performance. In particular, a composition according to the invention is stable and makes it possible to mask the imperfections and to provide a radiant complexion, while at the same time having good sensory properties, in particular in terms of emollience, tack and glide on the skin.

Preferably, a composition according to the invention comprises less than 2.0% by weight of silicone compound(s), in particular less than 1.0% by weight of silicone compound(s), preferably less than 0.5% by weight of silicone compound(s), relative to the total weight of the composition, and more preferentially is devoid (free) of silicone compound(s).

Preferably, a composition according to the invention comprises less than 2.0% by weight of silicone, in particular less than 1.0% by weight of silicone, preferably less than 0.5% by weight of silicone, relative to the total weight of the composition, and more preferentially is devoid (free) of silicone.

Preferably, a composition according to the invention comprises less than 2.0% by weight of microplastic compound(s), in particular less than 1.0% by weight of microplastic compound(s), preferably less than 0.5% by weight of microplastic compound(s), relative to the total weight of the composition, and more preferentially is devoid (free) of microplastic compound(s), in particular of microplastic filler(s).

Another subject of the invention, according to another of its aspects, is a cosmetic process for caring for keratin materials, in particular the skin and/or the lips, comprising at least one step of applying to said keratin materials a composition according to the invention.

DETAILED DESCRIPTION

As indicated above, according to a first aspect, the present invention relates to a composition, especially cosmetic composition, in particular for caring for keratin materials, comprising:

- at least one particulate cellulosic compound;
- at least hydrophobic silica aerogel particles; and
- at least one semicrystalline polymer containing at least one alkyl acrylate chain.

Particulate Cellulosic Compound

A composition according to the invention comprises at least one particulate cellulosic compound.

For the purposes of the invention, the term "particulate" means that the cellulosic compound is in the form of particles.

Thus, the particulate cellulosic compounds according to the invention differ from the polymeric celluloses.

The particulate cellulosic compounds are more particularly chosen from cellulosic compounds in the form of spheres, cellulosic compounds in the form of fibres, and mixtures thereof.

Among the spherical cellulose particles, mention may in particular be made of the following commercial products sold by the company Daito Kasei in Japan:

- Cellulobeads USF® with a particle size of 4-7 μm (porous spherical cellulose beads),
- Cellulobeads D-5® with a particle size of less than 10 μm,
- Cellulobeads D-10® with a particle size of 15 μm,
- Moiscell PW D-5 XP® with a particle size of 10 μm (potassium cellulose succinate),
- Moiscell PW D-50 XP® with a particle size of 50 μm (potassium cellulose succinate).

Among the cellulosic particles in the form of fibres, mention may in particular be made of:

- the cellulose fibres sold under the name Tego® Feel C 10, by the company Evonik, which have a mean particle size of 30 μm, and
- the cellulose fibres sold under the name Naturesoft® 800, by the company Micro Powders, which have a mean particle size of 7-12 μm.

The term "mean size" of the particles means the parameters D[4,3] and D[2,3] measured via the dry route by laser diffraction using a Microtrac S3500 particle size analyzer, the results being expressed in the form of the volume and number particle size distributions giving access to the mean diameter.

In a particular embodiment, the particulate cellulosic compounds according to the invention are chosen from cellulosic compounds in the form of spheres.

The cellulosic compounds in the form of spheres are preferably chosen from spherical cellulose beads and/or microcrystalline celluloses in the form of spheres, and more preferentially from spherical cellulose beads.

For the purposes of the invention, the term "cellulose beads" means cellulose particles in spherical form having a volume-median diameter of less than or equal to 8 μm.

The cellulose beads may be porous or nonporous.

Preferably, the cellulose beads are porous.

The porosity of the cellulose microbeads can be characterized by a specific surface area of from 10 $m^2/g$ to 1500 $m^2/g$, more preferentially of from 50 $m^2/g$ to 1000 $m^2/g$, and even more preferentially of from 50 $m^2/g$ to 500 $m^2/g$, according to the BET method.

As spherical cellulose beads, mention may preferably be made of those sold by the company Daito Kasei under the name Cellulobeads USF®.

In particular, a composition according to the invention comprises from 0.1% to 10% by weight, preferably from 0.5% to 5% by weight, and more preferentially from 0.5% to 3% by weight, of particulate cellulosic compound(s), and in particular spherical cellulose beads, relative to the total weight of the composition.

According to a particular embodiment, the compositions according to the invention comprise less than 0.5% by weight of polymeric cellulosic compound(s), in particular less than 0.1% by weight, and preferably are free of polymeric cellulosic compound(s).

Hydrophobic Silica Aerogel Particles

A composition according to the invention comprises hydrophobic silica aerogel particles.

Aerogels are ultralight porous materials which were first produced by Kristler in 1932.

The term "hydrophobic silica" means both pure hydrophobic silicas and particles completely or partially coated with hydrophobic silica.

Hydrophobic silicas that may be used are preferably amorphous and of fumed origin. They are preferably provided in pulverulent form.

The amorphous hydrophobic silicas of fumed origin are generally obtained from hydrophilic fumed silicas. The latter are obtained by pyrolysis of silicon tetrachloride ($SiCl_4$) in a continuous flame at 1000° C. in the presence of hydrogen and oxygen. They are subsequently rendered hydrophobic for example by treatment with halogenated silanes, alkoxysilanes or silazanes. The hydrophobic silicas differ from the starting hydrophilic silicas, inter alia, by a lower density of silanol groups and by a smaller adsorption of water vapour.

According to a particular embodiment, a composition according to the invention may comprise hydrophobically treated fumed silica aerogel particles.

The hydrophobic groups may be trimethylsiloxyl groups, which are obtained notably by treating fumed silica in the presence of hexamethyldisilazane, or else dimethylsilyloxyl groups, which are notably obtained by treating fumed silica in the presence of dimethyldichlorosilane.

The hydrophobic silica aerogel particles used according to the present invention are preferably silylated silica (INCI name: Silica Silylate) aerogel particles.

It will also be possible to use hydrophobic silica aerogel particles surface-modified with trimethylsilyl groups, namely trimethylsiloxylated silica particles.

The hydrophobic silica aerogel particles that may be used in the present invention preferably have a size, expressed as the mean diameter (D[0.5]), of less than 1500 μm, and preferably ranging from 1 μm to 30 μm, preferably from 2 μm to 25 μm, better still from 2 μm to 20 μm and even better still from 2 μm to 15 μm.

Use will preferably be made of the aerogel sold under the name VM-2270 (INCI name: Silica silylate) by the company Dow Corning, the particles of which have a mean size ranging from 5 microns to 15 microns and a specific surface area per unit mass ranging from 600 $m^2/g$ to 800 $m^2/g$.

As hydrophobic silica aerogels that may be used in the invention, mention may also be made of the aerogel sold under the name VM-2260 (INCI name: Silica silylate), by the company Dow Corning, the particles of which have a mean size of approximately 1000 microns and a specific surface area per unit mass ranging from 600 $m^2/g$ to 800 $m^2/g$.

As hydrophobic silica aerogels that may be used in the invention, mention may also be made of the aerogels sold by the company Cabot under the references Aerogel TLD 201, Aerogel OGD 201 and Aerogel TLD 203, Enova Aerogel MT 1100, and Enova Aerogel MT 1200, and also the references Airlica TL3 and Airlica TL5 sold by the company Toyukama.

A composition according to the invention comprises at least 0.1% by weight of hydrophobic silica aerogel particles, relative to the total weight of said composition.

In particular, a composition according to the invention comprises from 0.05% to 5% by weight, preferably from 0.1% to 2% by weight, and more preferentially from 0.1% to 0.8% by weight, of hydrophobic silica aerogel particles, relative to the total weight of the composition.

Semicrystalline Polymer Containing at Least One Alkyl Acrylate Chain

As indicated above, the composition according to the invention comprises at least one semicrystalline polymer containing at least one alkyl acrylate chain.

For the purposes of the invention, the term "semicrystalline polymer" is understood to mean polymers comprising a crystallizable portion, pendant chain or block in the backbone, and an amorphous portion in the backbone, and having a first-order reversible change of phase temperature, in particular melting point (solid-liquid transition).

When the crystallizable portion is a block of the polymer backbone, this crystallizable block is of different chemical nature from that of the amorphous blocks; the semicrystalline polymer is, in this case, a block polymer, for example of the diblock, triblock or multiblock type, comprising at least one crystallizable block and at least one amorphous block.

The term "block" is generally understood to mean at least 5 identical repeating units. The crystallizable block(s) is (are) then of different chemical nature from the 5 amorphous block(s).

Advantageously, the semicrystalline polymer containing at least one alkyl acrylate chain of the composition of the invention has an average molecular mass (Mn) of greater than or equal to about 2000 g/mol, preferably from about 2000 to 800 000 g/mol, preferably from about 3000 to 500 000 g/mol, preferably from about 4000 to 150 000 g/mol, and preferably from about 4000 to 99 000 g/mol.

Aside from the crystallizable chains or blocks, the blocks of the polymers are amorphous.

For the purposes of the invention, the term "crystallizable chain or block" is understood to mean a chain or block which, if it were alone, would change from the amorphous state to the crystalline state reversibly, depending on whether the temperature is above or below the melting point. For the purposes of the invention, a chain is a group of atoms, which is pendent or lateral relative to the polymer backbone. A block is a group of atoms belonging to the backbone, this group constituting one of the repeating units of the polymer. Advantageously, the "pendent crystallizable chain" may be a chain containing at least 6 carbon atoms.

Preferably, the polymer backbone of the semicrystalline polymers is soluble in the oily phase.

Thus, the semicrystalline polymer containing at least one alkyl acrylate chain that is used in the composition of the invention is generally introduced into the oily phase of the composition.

Preferably, the crystallizable blocks or chains of the semicrystalline polymers containing at least one alkyl acrylate chain represent at least approximately 30% by weight and preferably at least approximately 40% by weight relative to the total weight of each polymer.

The semicrystalline polymers comprising crystallizable blocks used according to the invention are block or multiblock polymers. They may be obtained by polymerizing monomers bearing reactive (or ethylenic) double bonds or by polycondensation. When the polymers of the invention are polymers bearing crystallizable side chains, these polymers are advantageously in random or statistical form.

The semicrystalline polymers of the invention may be of synthetic origin. Moreover, they do not comprise a polysaccharide backbone.

The semicrystalline polymers of the composition of the invention may or may not be partially crosslinked. It may then be a case of chemical crosslinking, by reaction with a multifunctional monomer during the polymerization. It may also be a case of physical crosslinking, which may then be due either to the establishment of bonds of hydrogen or dipolar type between groups borne by the polymer, such as dipolar interactions between carboxylate ionomers, these interactions being in small amount and borne by the polymer backbone; or due to a phase separation between the crystallizable blocks and the amorphous blocks borne by the polymer.

Preferably, the semicrystalline polymers containing at least one alkyl acrylate chain of the composition according to the invention are non-crosslinked.

As examples of semicrystalline polymers according to the invention containing at least one alkyl acrylate chain, mention may be made of those resulting from the polymerization of one or more saturated alkyl (meth)acrylates.

Preferably, the semicrystalline polymers bearing a crystallizable side chain are alkyl (meth)acrylate homopolymers, or copolymers of these monomers with a hydrophilic monomer.

According to a preferred embodiment of the invention, the semicrystalline polymer containing at least one alkyl acrylate chain is derived from a monomer bearing a crystallizable chain chosen from saturated alkyl (meth)acrylates and even more particularly poly(stearyl acrylate)s or poly (behenyl acrylate)s.

According to a particular embodiment of the invention, the semicrystalline polymer containing at least one alkyl acrylate chain is chosen from copolymers resulting from the polymerization of at least one monomer bearing a crystallizable chain and chosen from saturated alkyl (meth)acrylates.

According to a preferred embodiment, the semicrystalline polymer containing at least one alkyl acrylate chain is chosen from the homopolymers obtained by polymerization of a monomer chosen from alkyl acrylates and alkyl methacrylates and from the copolymers obtained by copolymerization of a monomer chosen from alkyl acrylates and alkyl methacrylates with a hydrophilic monomer, preferably N-vinylpyrrolidone or a hydroxyethyl (meth)acrylate, and mixtures thereof, more preferentially still a hydroxyethyl (meth) acrylate, and mixtures thereof.

As particular examples of semicrystalline polymers that can be used in the composition according to the invention, mention may be made of the homopolymers obtained by polymerization of a monomer chosen from alkyl acrylates and alkyl methacrylates, preferably from stearyl acrylates and behenyl acrylates, especially the polymers having the INCI name Poly C10-30 Alkyl Acrylate such as the Intelimer® products from the company Evonik, such as the product Intelimer® IPA 13-1, which is a polystearyl acrylate, or the product Intelimer® IPA 13-6, which is a behenyl polymer (polybehenyl acrylate), or else the Tego® SP products from the company Evonik.

As particular examples of semicrystalline polymers that can be used in the composition, mention may also be made of the copolymers obtained by copolymerization of a monomer chosen from alkyl acrylates and alkyl methacrylates with a hydrophilic monomer, preferably a hydroxyethyl (meth)acrylate, especially the copolymers described in applications FR 3 073 405 and FR 3 073 406, and preferably the copolymers obtained by copolymerization of at least one monomer chosen from alkyl acrylates, preferably from behenyl acrylates, stearyl acrylates, and mixtures thereof, with a hydrophilic monomer such as hydroxyethyl (meth) acrylate and N-vinylpyrrolidone, and preferably hydroxyethyl acrylate.

Preferably, the semicrystalline polymer containing at least one alkyl acrylate chain is a behenyl acrylate/2-hydroxyethyl acrylate copolymer, a stearyl acrylate/2-hydroxyethyl acrylate copolymer, and/or one of the mixtures thereof, and in particular the polymer having the INCI name: Poly C12-22 Alkyl Acrylate/Hydroxyethylacrylate Copolymer sold in particular under the name Tego SP Senstar by the company Evonik.

According to a preferred embodiment, the semicrystalline polymer(s) containing at least one alkyl acrylate chain are chosen from a polystearyl acrylate, a polybehenyl acrylate, a behenyl acrylate/2-hydroxyethyl acrylate copolymer, a stearyl acrylate/2-hydroxyethyl acrylate copolymer, and one of the mixtures thereof, in particular chosen from the polymer having the INCI name: Poly C10-30 Alkyl Acrylate, the copolymer having the INCI name C12-22 Alkyl Acrylate/Hydroxyethylacrylate Copolymer, and mixtures thereof, more particularly the polymer having the INCI name: Poly C10-30 Alkyl Acrylate.

According to a more preferred embodiment, the semicrystalline polymer containing at least one alkyl acrylate chain is a polymer having the INCI name: Poly C10-30 Alkyl Acrylate.

According to a more particular embodiment of the invention, the content of semicrystalline polymer(s) containing at least one alkyl acrylate chain ranges from 0.5% to 3% by weight, preferably from 0.5% to 2% by weight, relative to the total weight of the composition.

According to a more particular embodiment of the invention, the content of semicrystalline polymer(s) containing at least one alkyl acrylate chain ranges from 0.5% to 1.5% by weight, relative to the total weight of the composition.

Fatty Phase

A composition according to the invention may comprise at least one fatty phase.

For the purposes of the invention, the term "fatty phase" is understood to mean a phase comprising at least one oil and all of the liposoluble and lipophilic ingredients or fatty substances required according to the invention.

Thus, a composition according to the invention may comprise a fatty phase comprising, in addition to the semicrystalline polymer(s) suitable for use in the invention, at least one oil, in particular a cosmetic oil and where appropriate at least one additional wax and/or pasty substance.

In particular, a composition according to the invention may comprise from 0.5% to 50% by weight, preferably from 0.5% to 40% by weight of fatty phase, relative to the total weight of the composition.

Oils

The term "oil" is understood to mean a water-immiscible non-aqueous compound that is liquid at ambient temperature (20° C.) and atmospheric pressure (760 mmHg).

A fatty phase that is suitable for preparing the compositions, especially cosmetic compositions, according to the invention may comprise hydrocarbon-based oils, silicone oils, fluoro oils or non-fluoro oils, or mixtures thereof.

The oils may be volatile or non-volatile.

They may be of animal, plant, mineral or synthetic origin.

The fatty phase may comprise at least one volatile or non-volatile hydrocarbon-based oil and/or one volatile and/or non-volatile silicone oil and/or one volatile and/or non-volatile fluoro oil.

For the purposes of the present invention, the term "hydrocarbon-based oil" is understood to mean an oil mainly containing hydrogen and carbon atoms.

The term "silicone oil" is understood to mean an oil comprising at least one silicon atom and notably at least one Si—O group.

The term "fluoro oil" is understood to mean an oil comprising at least one fluorine atom.

The oils may optionally comprise oxygen, nitrogen, sulfur and/or phosphorus atoms, for example in the form of hydroxyl or acid radicals, provided that these oils are environmentally friendly.

Volatile Oils

For the purposes of the invention, the term "volatile oil" is understood to mean any oil that is capable of evaporating on contact with the skin in less than one hour, at ambient temperature and atmospheric pressure. The volatile oil is a volatile cosmetic compound, which is liquid at ambient temperature, having in particular a non-zero vapour pressure, at ambient temperature and atmospheric pressure, in particular having a vapour pressure ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The volatile oils may be hydrocarbon-based oils or silicone oils.

Among the volatile hydrocarbon-based oils containing from 8 to 16 carbon atoms, mention may be made notably of branched $C_8$-$C_{16}$ alkanes, for instance $C_8$-$C_{16}$ isoalkanes (also known as isoparaffins), isododecane, isodecane, isohexadecane and, for example, the oils sold under the trade names Isopar or Permethyl, branched $C_8$-$C_{16}$ esters, for instance isohexyl neopentanoate, and mixtures thereof.

Mention may also be made of volatile linear alkanes comprising from 8 to 16 carbon atoms, in particular from 10 to 15 carbon atoms, and more particularly from 11 to 13 carbon atoms, for instance n-dodecane ($C_{12}$) and n-tetradecane ($C_{14}$) sold by Sasol under the respective references Parafol 12-97 and Parafol 14-97, and also mixtures thereof, the undecane-tridecane mixture, mixtures of n-undecane ($C_{11}$) and of n-tridecane ($C_{13}$) obtained in examples 1 and 2 of patent application WO 2008/155059 from the company Cognis, and mixtures thereof.

Volatile silicone oils that may be mentioned include volatile linear silicone oils such as hexamethyldisiloxane, octamethyltrisiloxane, decamethyltetrasiloxane, tetradecamethylhexasiloxane, hexadecamethylheptasiloxane and dodecamethylpentasiloxane.

Volatile cyclic silicone oils that may be mentioned include hexamethylcyclotrisiloxane, octamethylcyclotetrasiloxane, decamethylcyclopentasiloxane, cyclohexasiloxane and dodecamethylcyclohexasiloxane, and in particular cyclohexasiloxane.

Use may also be made of volatile fluoro oils, such as nonafluoromethoxybutane, nonafluoromethoxybutane, decafluoropentane, tetradecafluorohexane, dodecafluoropentane, and mixtures thereof.

Non-Volatile Oils

The term "non-volatile" is understood to mean to an oil of which the vapour pressure at ambient temperature and atmospheric pressure is non-zero and is less than $10^{-3}$ mmHg (0.13 Pa).

The non-volatile oils may notably be chosen from non-volatile hydrocarbon-based, fluoro and/or silicone oils.

Non-volatile hydrocarbon-based oils that may notably be mentioned include:

- hydrocarbon-based oils of animal origin,
- linear or branched hydrocarbons of mineral or synthetic origin, such as petroleum jelly, polydecenes, hydrogenated polyisobutene such as Parleam, and squalane, and mixtures thereof,
- non-volatile alkanes, preferably with a viscosity of less than 20 mPa·s at 20° C. measured with a Rheomat RM100® viscometer from Lamy Rheology. The term "non-volatile alkane" is understood to mean a hydrocarbon-based cosmetic oil which is liquid at ambient temperature, notably having a vapour pressure at 20° C. of less than 0.01 kPa, according to the definition of a Volatile Organic Compound (VOC) of article 2 of European Council Directive 1999/13/EC of 11 Mar., 1992: "Any organic compound having, at a temperature of 293.15 K, a vapour pressure of 0.01 kPa or more". In particular, the non-volatile alkanes comprise from 10 to 30 carbon atoms, in particular from 12 to 26 carbon atoms, and more particularly from 15 to 19 carbon atoms, and preferably a mixture of alkanes containing from 15 to 19 carbon atoms, for example the products sold under the references Emogreen L19 and Emosmart L19 from SEPPIC,
- hydrocarbon-based oils of plant origin, such as glyceride triesters, which are generally triesters of fatty acids and of glycerol, the fatty acids of which may have varied chain lengths from 4 to 24 carbon atoms, it being possible for these chains to be saturated or unsaturated and linear or branched; these oils are notably wheatgerm oil, rice bran oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, sesame oil, marrow oil, rapeseed oil, blackcurrant oil, evening primrose oil, millet oil, barley oil, quinoa oil, rye oil, safflower oil, candlenut oil, passionflower oil, musk rose oil and Limnanthes alba seed oil (INCI name: Limnanthes Alba (Meadowfoam) Seed Oil); or else caprylic/capric acid triglycerides, such as those sold by the company Stdarinerie Dubois or those sold under the names Miglyol 810, 812 and 818 by the company Dynamit Nobel,
- synthetic ethers containing from 10 to 40 carbon atoms, such as dicapryl ether,
- synthetic esters, such as the oils of formula $R_1COOR_2$, in which $R_1$ represents a linear or branched fatty acid residue comprising from 1 to 40 carbon atoms and $R_2$ represents a hydrocarbon chain that is notably branched, containing from 1 to 40 carbon atoms, with the proviso that $R_1+R_2$ is greater than or equal to 10, for instance purcellin oil (cetostearyl octanoate), isopropyl myristate, myristyl myristate, isopropyl palmitate, alkyl benzoates having between 12 and 15 carbon atoms, such as the product sold under the trade name Finsolv TN or Witconol TN by the company Witco or Tegosoft TN by the company Evonik Goldschmidt, 2-ethylphenyl benzoate, such as the commercial product sold under the name X-Tend 226 by the company ISP, isopropyl lanolate, hexyl laurate, diisopropyl adipate, isononyl isononanoate, oleyl erucate, 2-ethylhexyl palmitate, isostearyl isostearate, diisopropyl sebacate such as the product sold under the name Dub Dis by the company Stéarinerie Dubois, alcohol or polyalcohol octanoates, decanoates or ricinoleates, such as propylene glycol dioctanoate; hydroxylated esters, such as isostearyl lactate, diisostearyl malate; and pentaerythritol esters, in particular pentaerythrityl tetraoctanoate (INCI name: Pentaerythrityl Tetraethylhexanoate); dipentaerythrityl hexacaprylate/hexacaprate, citrates, such as the ester of $C_3$-$C_{22}$ tricarboxylic acid and of $C_1$-$C_6$ alcohols with the INCI name Triethyl Citrate, for example the one sold under the name Citrofol AI Extra by the company Jungbunzlauer; tartrates, such as linear dialkyl tartrates having 12 or 13 carbon atoms, for example those sold under the name Cosmacol ETI by the company Enichem Augusta Industriale, and also linear dialkyl tartrates having between 14 and 15 carbon atoms, for example those sold under the name Cosmacol ETL by the same company, and acetates,
- polyol esters and pentaerythritol esters, for instance dipentaerythrityl tetrahydroxystearate/tetraisostearate,
- esters of diol dimer and diacid dimer, where appropriate esterified on their free alcohol or acid function(s) with acid or alcohol radicals, in particular dimer dilinoleate esters; more particularly chosen from the esters having the following INCI nomenclature: bis-behenyl/isostearyl/phytosteryl dimer dilinoleyl dimer dilinoleate (Plandool G), phytosteryl/isostearyl/cetyl/stearyl/behenyl dimer dilinoleate (Plandool H or Plandool S), and mixtures thereof, fatty amides, such as isopropyl N-lauroyl sarcosinate, for example the product sold under the trade name Eldew SL205 from Ajinomoto, fatty alcohols that are liquid at ambient temperature, with a branched and/or unsaturated carbon-based chain containing from 12 to 26 carbon atoms, for instance octyldodecanol, stearyl alcohol, oleyl alcohol, cetyl alcohol (2-hexyldecanol), 2-butyloctanol or 2-undecylpentadecanol, $C_{12}$-$C_{22}$ higher fatty acids, such as oleic acid, linoleic acid, linolenic acid, and mixtures thereof, carbonates, such as dicaprylyl carbonate, for example the product sold under the name Cetiol CC by the company Cognis;

non-phenyl silicone oils, for instance caprylyl methicone, and phenyl silicone oils, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, dimethicones or phenyl trimethicone with a viscosity of less than or equal to 100 cSt, trimethylpentaphenyltrisiloxane, and mixtures thereof;

and also mixtures of these various oils.

Other Fatty Substances

A fatty phase according to the invention may further comprise, mixed or dissolved in an oil, other fatty substances different from the semicrystalline polymer(s) suitable for use in the invention.

The other fatty substances which can be present in the oily phase are, for example:

fatty acids comprising from 8 to 30 carbon atoms, such as stearic acid, lauric acid, palmitic acid and oleic acid;

waxes, such as paraffin waxes, lignite waxes or microcrystalline waxes, ceresin or ozokerite, or synthetic waxes, such as polyethylene waxes or Fischer-Tropsch waxes;

silicone resins such as trifluoromethyl($C_1$-$C_4$)alkyl dimethicone and trifluoropropyl dimethicone;

silicone elastomers such as the products sold under the name KSG by the company Shin-Etsu, under the names Trefil or BY29 by the company Dow Corning or under the name Gransil by the company Grant Industries;

a gum chosen from silicone gums (dimethiconol);

a pasty compound, such as polymeric or non-polymeric silicone compounds, esters of an oligomeric glycerol, arachidyl propionate, fatty acid triglycerides and derivatives thereof;

and mixtures thereof.

As fatty substance, a composition according to the invention may in particular comprise at least one butter, in particular a plant butter.

The plant butter(s) suitable for use in the invention are preferably chosen from the group comprising avocado butter, cocoa butter, shea butter, in particular that having the INCI name Butyrospermum Parkii Butter, such as that sold under the reference Sheasoft® by the company Aarhuskarlshamn, kokum butter, mango butter, murumuru butter, coconut butter, apricot kernel butter, sal butter, urucum butter and mixtures thereof, and in particular is shea butter.

These fatty substances may be chosen in a varied manner by a person skilled in the art in order to prepare a composition having the desired properties, for example in terms of consistency or texture.

According to a preferred embodiment, a composition according to the invention comprises at least one non-volatile hydrocarbon-based oil, and preferably at least one non-volatile ester oil.

According to a preferred embodiment, a composition according to the invention comprises at least one non-volatile oil, preferably at least one non-volatile hydrocarbon-based oil, in particular chosen from linear or branched hydrocarbons of mineral or synthetic origin, hydrocarbon-based oils of plant origin, synthetic esters, esters of diol dimer and diacid dimer, fatty alcohols liquid at ambient temperature and having a branched and/or unsaturated carbon chain containing from 12 to 26 carbon atoms, carbonates, and also the mixtures of these various oils.

In particular, such non-volatile hydrocarbon-based oils may be present in a composition according to the invention in a content ranging from 0.1% to 40% by weight, in particular from 0.5% to 30%, preferably from 0.5% to 25% by weight, relative to the total weight of the composition.

According to a preferred embodiment, a composition according to the invention contains at least one oil chosen from squalane, glyceride triesters, myristyl myristate, isononyl isononanoate, pentaerythritol esters, in particular pentaerythrityl tetraoctanoate, dipentaerythrityl hexacaprylate/hexacaprate, dimer dilinoleate esters, in particular bis-behenyl/isostearyl/phytosteryl dimer dilinoleyl dimer dilinoleate, octyldodecanol, stearyl alcohol, cetyl alcohol, dicaprylyl carbonate, and mixtures thereof.

Preferably, a composition according to the invention comprises a fatty phase containing at least one other fatty substance, different from the semicrystalline polymer(s) suitable for use in the invention, in particular at least one butter, more particularly a plant butter, and preferably shea butter.

Preferably, a composition according to the invention comprises a fatty phase containing at least one non-volatile hydrocarbon-based oil, and preferably at least one fatty alcohol that is liquid at ambient temperature with a branched and/or unsaturated carbon-based chain containing from 12 to 26 carbon atoms.

More preferentially, a composition according to the invention comprises a fatty phase containing at least octyldodecanol, cetyl alcohol (2-hexyldecanol), or mixtures thereof.

Preferably, the fatty phase content is between 0.5% and 50% by weight, in particular between 0.5% and 40% by weight, relative to the total weight of the composition.

Preferably, a composition according to the invention comprises less than 2.0% by weight of silicone oil(s), in particular less than 1.0% by weight of silicone oil(s), preferably less than 0.5% by weight of silicone oil(s), relative to the total weight of the composition, and more preferentially is devoid (free) of silicone oil(s).

Aqueous Phase

According to a particular embodiment, a composition according to the invention may comprise at least one aqueous phase.

When present, the aqueous phase of a composition according to the invention comprises water and optionally a water-soluble solvent.

In particular, a composition according to the invention may comprise from 50% to 99.5% by weight and preferably from 60% to 99.5% by weight of water, relative to the total weight of the composition.

In particular, a composition according to the invention may comprise from 50% to 99.5% by weight and preferably from 60% to 99.5% by weight of aqueous phase, relative to the total weight of the composition.

In the present invention, the term "water-soluble solvent" denotes a compound which is liquid at ambient temperature and miscible with water (miscibility in water of greater than 50% by weight at 25° C. and atmospheric pressure).

The water-soluble solvents that can be used in the composition of the invention may also be volatile.

Among the water-soluble solvents that may be used in the composition in accordance with the invention, mention may be made especially of lower monoalcohols containing from 1 to 5 carbon atoms, such as ethanol and isopropanol, $C_3$ and $C_4$ ketones and $C_2$-$C_4$ aldehydes.

According to a variant embodiment, the aqueous phase of a composition according to the invention may comprise at least one $C_2$-$C_{32}$ polyol.

For the purposes of the present invention, the term "polyol" should be understood as meaning any organic molecule comprising at least two free hydroxyl groups.

Preferably, a polyol in accordance with the present invention is present in liquid form at ambient temperature.

A polyol that is suitable for use in the invention may be a compound of linear, branched or cyclic, saturated or unsaturated alkyl type, bearing on the alkyl chain at least two —OH functions, in particular at least three —OH functions and more particularly at least four —OH functions.

The polyols that are advantageously suitable for formulating a composition according to the present invention are those notably containing from 2 to 32 carbon atoms and preferably 3 to 16 carbon atoms.

Advantageously, the polyol may, for example, be chosen from ethylene glycol, pentaerythritol, trimethylolpropane, propylene glycol, dipropylene glycol, 1,3-propanediol, caprylyl glycol, butylene glycol, isoprene glycol, pentylene glycol, hexylene glycol, glycerol, polyglycerols, such as glycerol oligomers, for instance diglycerol, polyethylene glycols, and mixtures thereof.

According to a preferred embodiment of the invention, said polyol is chosen from caprylyl glycol, butylene glycol, glycerol, and mixtures thereof.

According to a preferred embodiment of the invention, said polyol is chosen from butylene glycol, glycerol, and mixtures thereof.

According to another preferred embodiment of the invention, the composition of the invention may comprise at least glycerol.

According to a particular embodiment, a composition according to the invention may be anhydrous.

For the purposes of the present invention, the term "anhydrous composition" is understood to mean a composition with a water (or aqueous phase) content of less than 5% by weight, preferably less than 2% by weight and more preferably still less than 1% by weight relative to the weight of said composition, or alternatively even less than 0.5% and especially free of water. In this definition, the water mentioned includes the residual water provided by the mixed ingredients.

Gelling Agents

A composition according to the invention may comprise at least one gelling agent, and in particular at least one hydrophilic gelling agent.

For the purposes of the present invention, "hydrophilic gelling agent" is understood to mean a compound capable of gelling the aqueous phase of the compositions according to the invention.

The gelling agent is hydrophilic and is thus present in the aqueous phase of the composition.

The gelling agent may be water-soluble or water-dispersible.

The hydrophilic gelling agent may be chosen from synthetic polymeric gelling agents, polymeric gelling agents that are natural or of natural origin, mixed silicates and fumed silicas, and mixtures thereof.

Preferably, the hydrophilic gelling agent may be chosen from synthetic polymeric gelling agents, polymeric gelling agents that are natural or of natural origin, and mixtures thereof.

More preferentially, the hydrophilic gelling agent may be chosen from synthetic polymeric gelling agents.

Polymeric Gelling Agents that are Natural or of Natural Origin

The polymeric hydrophilic gelling agents that are suitable for use in the invention may be natural or of natural origin.

For the purposes of the invention, the term "of natural origin" is intended to denote polymeric gelling agents obtained by modification of natural polymeric gelling agents.

These gelling agents may be particulate or non-particulate.

More specifically, these gelling agents fall within the category of polysaccharides.

In particular, the polysaccharides may be chosen from fructans, gellans, glucans, amylose, amylopectin, glycogen, pullulan, dextrans, celluloses and derivatives thereof, in particular methylcelluloses, hydroxyalkylcelluloses, ethylhydroxyethylcelluloses and carboxymethylcelluloses, mannans, xylans, lignins, arabans, galactans, galacturonans, alginate-based compounds, chitin, chitosans, glucuronoxylans, arabinoxylans, xyloglucans, glucomannans, pectic acids and pectins, arabinogalactans, carrageenans, agars, glycosaminoglucans, acacia gums, tragacanth gums, ghatti gums, karaya gums, locust bean gums, galactomannans such as guar gums and nonionic derivatives thereof, in particular hydroxypropyl guar, and ionic derivatives thereof, biopolysaccharide gums of microbial origin, in particular scleroglucan or xanthan gums, mucopolysaccharides, and in particular chondroitin sulfates, and mixtures thereof, and preferably from biopolysaccharide gums of microbial origin.

Synthetic Polymeric Gelling Agents

For the purposes of the invention, the term "synthetic" means that the polymer is neither naturally existing nor a derivative of a polymer of natural origin.

The synthetic polymeric hydrophilic gelling agent under consideration according to the invention may or may not be particulate.

For the purposes of the invention, the term "particulate" means that the polymer is in the form of particles, preferably spherical particles.

As emerges from the text hereinbelow, the polymeric hydrophilic gelling agent is advantageously chosen from polyacrylamides and crosslinked and/or neutralized 2-acrylamido-2-methylpropanesulfonic acid polymers and copolymers; modified or unmodified carboxyvinyl polymers, and mixtures thereof, especially as defined below.

Polyacrylamides and 2-Acrylamido-2-Methylpropanesulfonic Acid Polymers and Copolymers The polymers used that are suitable as aqueous gelling agent for the invention may be crosslinked or non-crosslinked homopolymers or copolymers including at least the 2-acrylamido-2-methylpropanesulfonic acid (AMPS®) monomer, in a form partially or totally neutralized with a mineral base other than aqueous ammonia, such as sodium hydroxide or potassium hydroxide.

They are preferably completely or virtually completely neutralized, that is to say at least 90% neutralized.

These AMPS® polymers according to the invention may be crosslinked or non-crosslinked. The AMPS® polymers that are suitable for use in the invention are water-soluble or water-dispersible. In this case, they are either "homopolymers" comprising only AMPS® monomers and, if they are crosslinked, one or more crosslinking agents, or are copolymers obtained from AMPS® and one or more hydrophilic or hydrophobic ethylenically unsaturated monomers and, if they are crosslinked, one or more crosslinking agents. When said copolymers comprise hydrophobic ethylenically unsaturated monomers, these monomers do not comprise a fatty chain and are preferably present in small amounts.

Mention may be made, as water-soluble or water-dispersible AMPS® homopolymers suitable for use in the invention, for example, of crosslinked or non-crosslinked polymers of sodium acrylamido-2-methylpropanesulfonate, such as that used in the commercial product Simulgel 800 (CTFA name: Sodium Polyacryloyldimethyl Taurate), crosslinked polymers of ammonium acrylamido-2-methylpropanesulfonate (INCI name: Ammonium Polyacryldimethyltauramide) such as those described in patent EP 0 815 928 B1 and such as the product sold under the trade name Hostacerin AMPS® by the company Clariant.

Preferably, a composition according to the invention comprises an AMPS® homopolymer.

As water-soluble or water-dispersible AMPS® copolymers in accordance with the invention, examples that may be mentioned include:

- crosslinked acrylamide/sodium acrylamido-2-methylpropanesulfonate copolymers, such as that used in the commercial product Sepigel 305 (CTFA name: Polyacrylamide/$C_{13}$-$C_{14}$ Isoparaffin/Laureth-7) or that used in the commercial product sold under the name Simulgel 600 (CTFA: Acrylamide/Sodium Acryloyldimethyltaurate/Isohexadecane/Polysorbate-80) by the company SEPPIC;
- copolymers of AMPS® and of vinylpyrrolidone or vinylformamide, such as that used in the commercial product sold under the name Aristoflex AVC® by Clariant (CTFA name: Ammonium Acryloyldimethyltaurate/VP Copolymer) but neutralized by sodium hydroxide or potassium hydroxide;
- copolymers of AMPS® and of sodium acrylate, for instance the AMPS®/sodium acrylate copolymer, such as that used in the commercial product sold under the name Simulgel EG® by SEPPIC or under the trade name Sepinov EM (CTFA name: Hydroxyethyl Acrylate/Sodium Acryloyldimethyltaurate Copolymer);
- copolymers of AMPS® and of hydroxyethyl acrylate, for instance the AMPS®/hydroxyethyl acrylate copolymer, such as that used in the commercial product sold under the name Simulgel NS® by SEPPIC (CTFA name: Hydroxyethyl Acrylate/Sodium Acryloyldimethyltaurate Copolymer (and) Squalane (and) Polysorbate 60), or such as the product sold under the name sodium acrylamido-2-methylpropanesulfonate/hydroxyethyl acrylate copolymer, such as the commercial product Sepinov EMT 10 (INCI name: Hydroxyethyl Acrylate/Sodium Acryloyldimethyltaurate Copolymer).

As preferred water-soluble or water-dispersible AMPS® copolymers in accordance with the invention, mention may be made of crosslinked acrylamide/sodium acrylamido-2-methylpropanesulfonate copolymers and/or copolymers of AMPS® and of hydroxyethyl acrylate.

Modified or Unmodified Carboxyvinyl Polymers

The modified or unmodified carboxyvinyl polymers may be copolymers derived from the polymerization of at least one monomer (a) chosen from α,β-ethylenically unsaturated carboxylic acids or esters thereof, with at least one ethylenically unsaturated monomer (b) comprising a hydrophobic group. The term "copolymers" means both copolymers obtained from two types of monomer and those obtained from more than two types of monomer, such as terpolymers obtained from three types of monomer. According to a preferred embodiment, these polymers are crosslinked.

Among these polymers, the ones that are preferred according to the present invention are acrylate/$C_{10}$-$C_{30}$-alkyl acrylate copolymers (INCI name: Acrylates/$C_{10-30}$ Alkyl acrylate Crosspolymer) such as the products sold by the company Lubrizol under the trade names Pemulen TR-1, Pemulen TR-2, Carbopol 1382, Carbopol EDT 2020 and Carbopol Ultrez 20 Polymer, and even more preferentially Pemulen TR-2.

Among the modified or unmodified carboxyvinyl polymers, mention may also be made of sodium polyacrylates, such as those sold under the name Cosmedia SP® or Cosmedia SPL®, sold by the company Cognis.

Mention may also be made of partially neutralized sodium polyacrylates that are in the form of an inverse emulsion comprising at least one polar oil, for example the product sold under the name Luvigel® EM by the company BASF.

The modified or unmodified carboxyvinyl polymers may also be chosen from crosslinked (meth)acrylic acid homopolymers. For the purposes of the present patent application, the term "(meth)acrylic" is understood to mean "acrylic or methacrylic". Examples that may be mentioned include the products sold by Lubrizol under the names Carbopol 910, 934, 940, 941, 934 P, 980, 981, 2984, 5984 and Carbopol Ultrez 10 Polymer, or by 3V-Sigma under the name Synthalen® K, Synthalen® L or Synthalen® M.

Among the modified or unmodified carboxyvinyl polymers, mention may be made in particular of Carbopol (CTFA name: carbomer) and Pemulen (CTFA name: Acrylates/$C_{10-30}$ alkyl acrylate crosspolymer) sold by the company Lubrizol.

Surfactants

According to a preferred embodiment, the composition according to the invention may also comprise at least one surfactant.

The surfactants may be chosen from nonionic, anionic, cationic and amphoteric surfactants, and mixtures thereof. Reference may be made to the *Kirk-Othmer Encyclopedia of Chemical Technology*, volume 22, pages 333-432, 3rd Edition, 1979, Wiley, for the definition of the emulsifying properties and functions of surfactants, in particular pages 347-377 of this reference, for anionic, amphoteric and nonionic surfactants.

Nonionic Surfactant

Preferably, the composition according to the invention comprises at least one nonionic surfactant.

The nonionic surfactants may in particular be chosen from alkyl and polyalkyl esters of poly(ethylene oxide), oxyalkylenated alcohols, alkyl and polyalkyl ethers of poly(ethylene oxide), optionally polyoxyethylenated alkyl and polyalkyl esters of sorbitan, optionally polyoxyethylenated alkyl and polyalkyl ethers of sorbitan, alkyl and polyalkyl glycosides or polyglycosides, in particular alkyl and polyalkyl glucosides or polyglucosides, alkyl and polyalkyl esters of sucrose, in particular sucrose stearate, glyceryl esters, optionally polyoxyethylenated alkyl and polyalkyl esters of glycerol, optionally polyoxyethylenated alkyl and polyalkyl ethers of glycerol, gemini surfactants, cetyl alcohol, stearyl alcohol, nonionic triblock poly(ethylene glycol)-block-poly (propylene glycol)-block-poly(ethylene glycol) copolymers, also referred to as poloxamers, and mixtures thereof.

As glyceryl esters, mention may notably be made of $C_{16}$-$C_{22}$ fatty acid esters of glycerol, in particular glyceryl esters of a fatty acid having 18 carbon atoms, and polyglyceryl esters of a fatty acid containing from 8 to 20 carbon atoms.

Glyceryl esters of a Cis fatty acid that may notably be mentioned include glyceryl stearate (glyceryl monostearate, distearate and/or tristearate) (CTFA name: glyceryl stearate), glyceryl ricinoleate, or mixtures thereof.

As fatty acid ester of glycerol, mention may be made of mixtures based on glyceryl stearate, such as the mixture of glyceryl stearate and polyethylene glycol 100 OE monostearate, and in particular the one comprising a 50/50 mixture, sold under the name Arlacel 165© by the company Croda, or else the product containing glyceryl stearate (glyceryl mono-distearate) and potassium stearate, sold under the name Tegin® by the company Goldschmidt (CTFA name: glyceryl stearate SE).

Preferably, a composition according to the invention comprises at least one surfactant, in particular a nonionic surfactant, and preferably a surfactant chosen from fatty acid esters of glycerol, nonionic triblock poly(ethylene glycol)-block-poly(propylene glycol)-block-poly(ethylene glycol) copolymers, and mixtures thereof.

Among the nonionic triblock poly(ethylene glycol)-block-poly(propylene glycol)-block-poly(ethylene glycol) copolymers, also referred to as poloxamers, mention may in particular be made of those sold under the name Pluronic or Kolliphor by the company BASF or else under the name of Synperonic by the company Croda.

Anionic Surfactant

The anionic surfactants may be chosen from alkyl ether sulfates, carboxylates, amino acid derivatives, sulfonates, isethionates, taurates, sulfosuccinates, alkyl sulfoacetates, phosphates and alkyl phosphates, polypeptides, metal salts of $C_{10}$-$C_{30}$ and notably $C_{16}$-$C_{25}$ fatty acids, in particular metal stearates and behenates, alkali metal salts of cetyl phosphate, and mixtures thereof.

As alkali metal salts of cetyl phosphate, mention may notably be made of potassium cetyl phosphate. Use may notably be made of the monopotassium salt of monocetyl phosphate (INCI name: potassium cetyl phosphate) sold under the name "Amphisol K" by the company DSM Nutritional Products.

Cationic Surfactant

The cationic surfactants may be chosen from alkylimidazolidiniums, such as isostearyl ethylimidonium ethosulfate, ammonium salts such as ($C_{12-30}$-alkyl)-tri($C_{1-4}$-alkyl)ammonium halides such as N,N,N-trimethyl-1-docosanaminium chloride (or behentrimonium chloride).

Amphoteric Surfactant

The compositions according to the invention may also contain one or more amphoteric surfactants, for instance N-acylamino acids such as N-alkyl aminoacetates and disodium cocoamphodiacetate, and amine oxides such as stearamine oxide, or alternatively silicone surfactants, for instance dimethicone copolyol phosphates such as the product sold under the name Pecosil PS 100® by the company Phoenix Chemical.

Silicone Surfactant

The composition may also comprise at least one silicone surfactant. By way of example, as nonionic surfactants with an HLB of greater than or equal to 8 at 25° C., used alone or as a mixture, mention may be made of dimethicone copolyol or dimethicone copolyol benzoate, and as nonionic surfactants with an HLB of less than 8 at 25° C., used alone or as a mixture, mention may be made of the cyclomethicone/dimethicone copolyol mixture.

Preferably, a composition according to the invention comprises less than 2% by weight of silicone surfactant(s), in particular less than 1% by weight of silicone surfactant(s), preferably less than 0.5% by weight of silicone surfactant(s) and more preferentially is devoid of silicone surfactant(s).

The surfactant(s) may be present in a composition according to the invention in a proportion ranging from 0.5% to 10% by weight and preferably from 0.5% to 6% by weight, relative to the total weight of the composition.

Active Agents

According to a preferred embodiment, a composition according to the invention may also comprise at least one additional cosmetic active agent.

In particular, the additional cosmetic active agent may be at least one hydrophilic active agent.

The term "hydrophilic active agent" means a water-soluble or water-dispersible active agent which is capable of forming hydrogen bonds.

As hydrophilic active agents, examples that may be mentioned include moisturizers, preferably glycerol, depigmenting agents, desquamating agents, humectants, anti-ageing agents; mattifying agents, cicatrizing agents, antibacterial agents, vitamins, preferably tocopherol, and mixtures thereof.

The additional active agent(s) may notably be chosen from:

- vitamins and derivatives thereof, notably esters thereof, such as tocopherol (vitamin E) and esters thereof (for instance tocopheryl acetate), ascorbic acid (vitamin C) and derivatives thereof, panthenol, niacinamide or vitamin B3;
- humectants, such as urea, hydroxyureas, glycerol, polyglycerols, glyceryl glucoside, diglyceryl glucoside, polyglyceryl glucosides and xylityl glucoside, and in particular glycerol;
- C-glycoside compounds, and preferably hydroxypropyl tetrahydropyrantriol, in particular sold under the name Mexoryl SBB® or Mexoryl SCN® by Chimex;
- antioxidant compounds;
- known anti-ageing active agents, such as hyaluronic acid compounds, and notably sodium hyaluronate, retinol and derivatives thereof, salicylic acid compounds and in particular 5-n-octanoylsalicylic acid (capryloylsalicylic acid), caffeine, adenosine, c-β-d-xylopyranoside-2-hydroxypropane and the sodium salt of (3-hydroxy-2-pentylcyclopentyl)acetic acid;
- organic or inorganic, insoluble or soluble, lipophilic or hydrophilic or particulate sunscreens.

The UV-screening agent is a UV-screening agent normally used in cosmetics. It may be chosen from the positive list contained in Annex VI of Regulation (EC) No 1223/2009, which specifies the list of UV-screening agents permitted in cosmetics.

The UV-screening agents suitable for use in the invention may be of various natures.

They may be lipophilic, hydrophilic or insoluble organic agents.

The term "lipophilic UV-screening agent" means any cosmetic or dermatological screening agent that can be fully dissolved in molecular form in a liquid fatty phase or that can be dissolved in colloidal form (for example in micellar form) in a liquid fatty phase.

The term "hydrophilic UV-screening agent" means any cosmetic or dermatological screening agent that can be fully dissolved in molecular form in a liquid aqueous phase or that can be dissolved in colloidal form (for example in micellar form) in a liquid aqueous phase.

The term "insoluble UV-screening agent" means any cosmetic or dermatological screening agent which is not defined either as a lipophilic UV-screening agent or as a hydrophilic UV-screening agent, and which is in the form of particles in aqueous phase or liquid fatty phase.

The UV-screening agents under consideration according to the invention may afford UVA and/or UVB photoprotection.

According to a preferred embodiment, a composition, preferably a cosmetic composition, according to the invention may comprise at least one organic and/or mineral UV-screening agent (agent which screens out the UV radiation of sunlight).

In particular, a composition according to the invention may comprise at least one UV-screening agent chosen from hydrophilic organic UV-screening agents, lipophilic organic UV-screening agents, insoluble organic UV-screening agents, mineral screening agents, and mixtures thereof.

In particular, a composition may comprise one or more UV-screening agents chosen from bis-resorcinyl triazine derivatives, dibenzoylmethane derivatives, benzylidenecamphor derivatives, and mixtures thereof.

The organic UV-screening agents may also be chosen from anthranilics; cinnamic derivatives; salicylic derivatives; benzophenone derivatives; phenylbenzotriazole derivatives; benzalmalonate derivatives, notably those mentioned in patent U.S. Pat. No. 5,624,663; phenylbenzimidazole derivatives; imidazolines; 4,4-diarylbutadiene derivatives; bisbenzazolyl derivatives, as described in patents EP 6 693 23 and U.S. Pat. No. 2,463,264; p-aminobenzoic acid (PABA) derivatives; methylenebis(hydroxyphenylbenzotriazole) derivatives as described in applications U.S. Pat. Nos. 5,237,071, 5,166,355, GB 2 303 549, DE 197 26 184 and EP 893 119; benzoxazole derivatives, as described in patent applications EP 0 832 642, EP 1 027 883, EP 1 300 137 and DE 101 62 844; screening polymers and screening silicones such as those described notably in application WO 93/04665; α-alkylstyrene-based dimers, such as those described in patent application DE 198 55 649; 4,4-diarylbutadienes as described in applications EP 0 967 200, DE 197 46 654, DE 197 55 649, EP 1 008 586, EP 1 133 980 and EP 133 981; merocyanine derivatives described in applications WO 04/006878, WO 05/058269 and WO 06/032741; and mixtures thereof.

According to a particular embodiment, the concentration of organic UV-screening agents in a composition according to the invention ranges from 1% to 50%, preferably from 1% to 40% by weight, and for example ranges from 5% to 35% by weight, relative to the total weight of the composition.

A composition according to the invention may also comprise mineral UV-screening agents, which are generally pigments. The pigments may or may not be coated.

The coated pigments are pigments that have undergone one or more surface treatments of chemical, electronic, mechanochemical and/or mechanical nature with compounds as described, for example, in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminium salts of fatty acids, metal alkoxides (titanium or aluminium alkoxides), polyethylene, silicones, proteins (collagen, elastin), alkanolamines, silicon oxides, metal oxides or sodium hexametaphosphate.

As is known, silicones are organosilicon polymers or oligomers comprising a linear or cyclic and branched or crosslinked structure, of variable molecular weight, obtained by polymerization and/or polycondensation of suitably functionalized silanes and essentially constituted of a repetition of main units in which the silicon atoms are connected to each other via oxygen atoms (siloxane bond), optionally substituted hydrocarbon-based radicals being connected directly to said silicon atoms via a carbon atom.

The term "silicones" also encompasses the silanes required for their preparation, in particular alkylsilanes.

The silicones used for coating the pigments that are suitable for the present invention are preferably chosen from the group containing alkylsilanes, polydialkylsiloxanes and polyalkylhydrosiloxanes. More preferentially still, the silicones are chosen from the group containing octyltrimethylsilane, polydimethylsiloxanes and polymethylhydrosiloxanes.

Needless to say, before being treated with silicones, the metal oxide pigments may have been treated with other surface agents, in particular with cerium oxide, alumina, silica, aluminium compounds or silicon compounds, or mixtures thereof.

Thus, the mineral UV-screening agents may be chosen from coated or uncoated pigments, and in particular from coated titanium oxide pigments, silicone-treated titanium oxides, uncoated titanium oxide pigments, uncoated zinc oxide pigments, coated zinc oxide pigments, uncoated cerium oxide pigments, uncoated iron oxide pigments, coated iron oxide pigments, and mixtures thereof.

Mention may also be made of mixtures of metal oxides, in particular of titanium dioxide and of cerium dioxide, including the equal-weight mixture of titanium dioxide and cerium dioxide coated with silica, sold by the company Ikeda under the name Sunveil A, and also the mixture of titanium dioxide and zinc dioxide coated with alumina, silica and silicone, such as the product M 261 sold by the company Kemira, or coated with alumina, silica and glycerol, such as the product M 211 sold by the company Kemira.

According to a particular embodiment, the amount of the mineral UV-screening agent(s) present in a composition according to the invention may range from 0.01% to 20% by weight, relative to the total weight of the composition. It ranges, for example, from 1% to 15% by weight, relative to the total weight of the composition.

According to a particular embodiment, the composition according to the invention also comprises one or more organic UV-screening agents and one or more mineral UV-screening agents.

According to a particular embodiment, a composition according to the invention may comprise a combination of UV-screening agents as described in patent FR 2 977 490, application WO 2013/004777 or application US 2014/0134120.

veinotonics, such as polyphenols, and notably escin, ruscus, diosmin, hesperidin, resveratrol, and mixtures thereof.

A composition according to the invention may comprise at least one moisturizer (also known as a humectant), in particular for a care application.

Preferably, the moisturizer is glycerol.

The moisturizer(s) may be present in the composition in a content ranging from 0.1% to 30% by weight, especially from 0.5% to 20% by weight or even from 1% to 12% by weight, relative to the total weight of said composition.

Preferably, a composition according to the invention may comprise at least one active agent, in particular chosen from anti-ageing agents, moisturizers, preferably glycerol, vitamins, preferably tocopherol, and mixtures thereof.

Such active agents may be present in a composition according to the invention in a content ranging from 0.15% to 35.0% by weight and preferably from 0.6% to 23% by weight, or even from 1.1% to 15% by weight, relative to the total weight of the composition.

C-Glycoside Compounds

In particular, the composition according to the invention may comprise at least one additional cosmetic active agent chosen from C-glycoside compounds, in particular of the following general formula:

[Chem. 1]

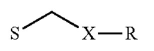

in which:

- R denotes an unsubstituted linear $C_1$-$C_4$ and notably $C_1$-$C_2$ alkyl radical, in particular methyl;
- S represents a monosaccharide chosen from D-glucose, D-xylose, N-acetyl-D-glucosamine and L-fucose, and in particular D-xylose;
- X represents a group chosen from —CO—, —CH(OH)— and —CH($NH_2$)— and preferentially a —CH(OH)— group;

and also the cosmetically acceptable salts thereof, solvates thereof such as hydrates, and optical isomers thereof.

As non-limiting illustrations of C-glycosides that are more particularly suitable for use in the invention, mention may notably be made of the following compounds:

C-β-D-xylopyranoside-n-propan-2-one;
C-α-D-xylopyranoside-n-propan-2-one;
C-β-D-xylopyranoside-2-hydroxypropane;
C-α-D-xylopyranoside-2-hydroxypropane;
1-(C-β-D-glucopyranosyl)-2-hydroxypropane;
1-(C-α-D-glucopyranosyl)-2-hydroxypropane;
1-(C-β-D-glucopyranosyl)-2-aminopropane;
1-(C-α-D-glucopyranosyl)-2-aminopropane;
3'-(acetamido-C-β-D-glucopyranosyl)propan-2'-one;
3'-(acetamido-C-α-D-glucopyranosyl)propan-2'-one;
1-(acetamido-C-β-D-glucopyranosyl)-2-hydroxypropane;
1-(acetamido-C-β-D-glucopyranosyl)-2-aminopropane;

and also the cosmetically acceptable salts thereof, solvates thereof such as hydrates, and optical isomers thereof.

According to a particular embodiment, use is made of C-β-D-xylopyranoside-2-hydroxypropane or C-α-D-xylopyranoside-2-hydroxypropane, and better still C-β-D-xylopyranoside-2-hydroxypropane.

According to a particular embodiment, a C-glycoside of the formula illustrated above that is suitable for use in the invention may preferably be C-β-D-xylopyranoside-2-hydroxypropane, the INCI name of which is Hydroxypropyl Tetrahydropyrantriol, notably sold under the name Mexoryl SBB® or Mexoryl SCN® by Chimex.

The C-glycoside salts that are suitable for use in the invention may comprise conventional physiologically acceptable salts of these compounds, such as those formed from organic or inorganic acids.

Examples that may be mentioned include the salts of mineral acids, such as sulfuric acid, hydrochloric acid, hydrobromic acid, hydriodic acid, phosphoric acid and boric acid. Mention may also be made of the salts of organic acids, which may include one or more carboxylic, sulfonic or phosphonic acid groups. They may be linear, branched or cyclic aliphatic acids, or alternatively aromatic acids. These acids may also include one or more heteroatoms chosen from O and N, for example in the form of hydroxyl groups. Mention may notably be made of propionic acid, acetic acid, terephthalic acid, citric acid and tartaric acid.

The solvates that are acceptable for the compounds described above comprise conventional solvates such as those formed during the final step of preparation of said compounds due to the presence of solvents. Examples that may be mentioned include solvates due to the presence of water or of linear or branched alcohols, such as ethanol or isopropanol.

The C-glycosides having the formula illustrated above are known from WO 02/051828.

Salicylic Acid Compounds

In particular, the composition according to the invention may comprise at least one additional cosmetic active agent chosen from salicylic acid compounds.

The salicylic acid compound present in the composition according to the invention is preferably chosen from salicylic acid and the compounds having the following formula:

[Chem. 2]

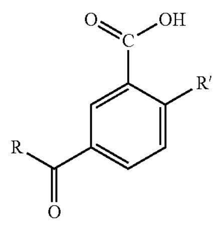

in which:

- the radical R denotes a linear, branched or cyclic saturated aliphatic chain containing from 2 to 22 carbon atoms; an unsaturated chain containing from 2 to 22 carbon atoms, containing one or more double bonds that may be conjugated; an aromatic nucleus linked to the carbonyl radical directly or via saturated or unsaturated aliphatic chains containing from 2 to 7 carbon atoms; said groups possibly being substituted with one or more substituents, which may be identical or different, chosen from (a) halogen atoms, (b) the trifluoromethyl group, (c) hydroxyl groups in free form or esterified with an acid containing from 1 to 6 carbon atoms, or (d) a carboxyl function in free form or esterified with a lower alcohol containing from 1 to 6 carbon atoms;
- R' is a hydroxyl group;

and also salts thereof derived from a mineral or organic base.

Preferentially, the radical R denotes a linear, branched or cyclic saturated aliphatic chain containing from 3 to 11 carbon atoms; an unsaturated chain containing from 3 to 17 carbon atoms and comprising one or more conjugated or unconjugated double bonds; said hydrocarbon-based chains possibly being substituted with one or more substituents, which may be identical or different, chosen from (a) halogen atoms, (b) the trifluoromethyl group, (c) hydroxyl groups in free form or esterified with an acid containing from 1 to 6 carbon atoms, or (d) a carboxyl function in free form or esterified with a lower alcohol containing from 1 to 6 carbon atoms; and salts thereof obtained by salification with a mineral or organic base.

The compounds that are more particularly preferred are those in which the radical R is a $C_3$-$C_{11}$ alkyl group.

Among the salicylic acid compounds that are particularly preferred, mention may be made of 5-n-octanoylsalicylic acid (or capryloylsalicylic acid); 5-n-decanoylsalicylic acid; 5-n-dodecanoylsalicylic acid; 5-n-heptanoylsalicylic acid, and the corresponding salts thereof.

The salicylic acid compound is preferably chosen from salicylic acid and 5-n-octanoylsalicylic acid, and more preferentially is 5-n-octanoylsalicylic acid.

The salts of the compounds having the formula illustrated above may be obtained by salification with a mineral or organic base. Examples of mineral bases that may be mentioned include alkali metal or alkaline-earth metal hydroxides, for instance sodium hydroxide or potassium hydroxide, or ammonia.

Among the organic bases, mention may be made of amines and alkanolamines. Quaternary salts, for instance those described in the patent FR 2 607 498, are particularly advantageous. The compounds having the formula illustrated above that may be used according to the invention are described in patents U.S. Pat. Nos. 6,159,479 and 5,558,871, FR 2 581 542, FR 2 607 498, U.S. Pat. No. 4,767,750, EP 378 936, U.S. Pat. Nos. 5,267,407, 5,667,789, 5,580,549 and EP-A-570 230.

A composition according to the invention may also include at least one additive chosen from the adjuvants conventionally used in the cosmetic field, such as preserving agents, fragrances, polar additives, film-forming polymers, pH modifiers (acids or bases), dispersants, cosmetic active agents, for instance cicatrizing agents, agents for combating greasy skin, and/or anti-pollution agents, and mixtures thereof.

A composition according to the invention may also include at least one pearlescent agent as additive. Among the pearlescent agents that can be envisioned, mention may in particular be made, by way of illustration and in nonlimiting fashion, of natural pearlescent agents, mica coated with titanium oxide, with iron oxide, with natural pigment or with bismuth oxychloride, and also coloured titanium mica, and mixtures thereof.

Needless to say, a person skilled in the art will take care to select this or these optional additional compound(s), and/or the amount thereof, such that the advantageous properties of a composition according to the invention are not, or are not substantially, adversely affected by the envisioned addition.

Cosmetic Composition

As stated previously, a composition according to the invention is preferably cosmetic.

A composition according to the invention is generally suitable for topical application to the skin and thus generally comprises a physiologically acceptable medium, i.e. a medium that is compatible with the skin.

It is preferably a cosmetically acceptable medium, i.e. a medium which has a pleasant colour, odour and feel and which does not cause any unacceptable discomfort, i.e. stinging, tautness or redness, liable to discourage the user from applying this composition.

A cosmetic composition according to the invention may be in any presentation form conventionally used in the cosmetic field according to the intended applications, in particular for topical application.

For topical application to keratin materials, and notably the skin or its integuments, a composition may notably be in the form of an aqueous or oily solution or of a dispersion of the lotion or serum type, of emulsions of liquid or semi-liquid consistency of the milk type, obtained by dispersing a fatty phase in an aqueous phase (oil-in-water) or conversely (water-in-oil), or of suspensions or emulsions of soft consistency of the aqueous or anhydrous gel or cream type, or else of microcapsules or microparticles, or of vesicular dispersions of ionic and/or nonionic type. These compositions are prepared according to the usual methods.

In particular, a composition according to the invention may be in the form of an emulsion, in particular an oil-in-water (O/W) or water-in-oil emulsion, in the form of an anhydrous composition, in the form of an aqueous composition, or in the form of a bi-gel (or gel-gel) composition. A gel-gel composition is different from an emulsion.

According to a particular embodiment, a composition according to the invention is an anhydrous composition.

According to another embodiment, a composition according to the invention is in the form of an emulsion; preferably, a composition according to the invention is in the form of an oil-in-water (O/W) emulsion.

Preferably, a composition according to the invention has a viscosity of between 3 Pa·s and 50 Pa·s, preferably of between 3.5 Pa·s and 20 Pa·s, measured using a Rheomat RM 200 rheometer from Lamy Rheology with a spindle that is suitable for the level of viscosity measured, for example at a speed of 200 rpm.

In particular, a composition according to the invention has a pH ranging from 3 to 8. Preferably, the pH of the composition ranges from 4 to 7.5.

A composition according to the invention may be characterized by haze and transparency (transmittance TH) measurements.

"Haze" corresponds to the percentage of light scattered relative to the total transmittance according to the standard ASTM D 1003 (Standard Test Method for Haze and Luminous Transmittance of Transparent Plastics).

50 μm films of composition are applied to 50 μm polyethylene (PE) films. The film is then measured after 1 hour of drying at ambient temperature. Finally, the film is placed in the machine and transparency and haze measurements are taken.

The measurements can be taken using a Hazegard instrument (Hazegard plus C©, BYKGardner).

According to a preferred embodiment, a composition according to the invention has a transmittance of greater than 85%, and more preferentially of greater than 90%.

According to a preferred embodiment, a composition according to the invention has a haze value at t=1 second of greater than 70%.

A composition according to the invention may be prepared according to the techniques that are well known to those skilled in the art.

According to a preferred embodiment, a composition of the invention may advantageously be in the form of a composition for caring for the skin and/or keratin fibres, especially the body or the face, in particular the face.

The compositions according to the invention have applications in a large number of treatments, in particular cosmetic treatments, of the skin, lips, in particular for protecting and/or caring for the skin, and/or lips, and/or for making up the skin and/or lips.

Another subject of the present invention is constituted of the use of the compositions according to the invention as defined above in the manufacture of products for the cosmetic treatment of keratin materials such as the skin, the lips, in particular of care products, sun protection and daily photoprotection products and makeup products.

The compositions according to the invention may be in the form of products for caring for the skin or semi-mucous membranes, such as a protective or cosmetic care composition for the face, for the lips, for the hands, for the feet, for the anatomical folds or for the body (for example, day creams, night cream, day serum, night serum, makeup-removing cream, makeup base, antisun composition, protective or care body milk, aftersun milk, skincare or scalp-care lotion, gel or foam, serum, mask, or aftershave composition).

The cosmetic compositions according to the invention may be used, for example, as care products and/or sun protection and daily photoprotection products for the face and/or the body, of liquid to semiliquid consistency, such as lotions, milks, more or less rich creams, gels and cream-gels. They may optionally be packaged in aerosol form and may be in the form of a foam or a spray.

In particular, a composition of the invention may advantageously be in the form of a composition for anti-ageing care of the skin of the body or the face, in particular the face.

According to another embodiment, a composition of the invention may be in the form of a makeup base composition.

According to an embodiment, a composition of the invention may advantageously be in the form of a product for the lips.

Such compositions are notably prepared according to the general knowledge of a person skilled in the art.

Preferably, the invention also relates to a cosmetic process for caring for keratin materials, in particular the skin and/or the lips, comprising at least one step of applying to said keratin materials a composition as defined above.

The composition may be applied to the skin by hand or using an applicator.

In particular, the compositions according to the invention may be applied directly to the skin or, alternatively, to cosmetic supports of occlusive or non-occlusive type, intended for example to be applied locally to the skin. As examples of cosmetic supports, mention may be made notably of a patch, a wipe, a roll-on, a mask or a pen.

Thus, the invention also relates to a cosmetic process for caring for keratin materials, in particular the skin and/or the lips, comprising at least one step of directly applying to said keratin materials a composition as defined above.

According to another embodiment, the invention also relates to a cosmetic process for caring for keratin materials, in particular the skin and/or the lips, comprising at least one step of applying a composition as defined above to cosmetic supports of occlusive or non-occlusive type, intended to be applied to said keratin materials, such as a patch, a wipe, a roll-on or a pen, and preferably a wipe.

In particular, a composition according to the invention may be used for combating the signs of skin ageing.

Thus, the present patent application also relates to the use of a composition according to the invention for combating the signs of skin ageing.

Specifically, a composition according to the present invention advantageously makes it possible to effectively reduce the visibility of wrinkles and fine lines.

The present invention also relates to the use of a composition according to the invention for improving the uniformity of the complexion, for reducing and/or preventing the characteristics of wrinkles and/or fine lines, for improving and/or reducing the microrelief of the skin, and/or for reducing and/or eliminating marks, and/or for making the skin smooth and/or for promoting desquamation of the skin and/or stimulating epidermal renewal.

Preferably, it relates to the cosmetic use of a composition according to the invention for reducing and/or preventing the appearance of wrinkles and/or fine lines, for improving and/or reducing the microrelief of the skin, and/or for making the skin smooth and/or for promoting desquamation of the skin and/or stimulating epidermal renewal.

Preferably, the present invention also relates to the use of a composition according to the invention for preventing and/or treating the appearance of wrinkles and/or fine lines.

Throughout the description, including the claims, the expression “comprising a” should be understood as being synonymous with “comprising at least one”, unless otherwise specified. The expressions “between . . . and . . . ”, “comprises from . . . to . . . ”, “formed of . . . to . . . ” and “ranging from . . . to . . . ” should be understood as including the limits, unless otherwise specified.

In the description and the examples, unless otherwise indicated, the percentages are percentages by weight (i.e. percentages by mass). The percentages are thus expressed by weight relative to the total weight of the composition. The temperature is expressed in degrees Celsius, unless otherwise indicated, and the pressure is atmospheric pressure, unless otherwise indicated.

The invention is illustrated in greater detail by the non-limiting examples presented below.

EXAMPLE

Measurement Methods

In the examples detailed below, the following measurement methods are used.

Protocol for Measuring the Soft-Focus Effect

The soft-focus effect is determined by measuring the haze and the transparency, i.e. the perception of light at wide angles.

The measurements are taken using a Hazegard instrument (Hazegard Plus C©, BYKGardner) on a film with a thickness of 50 μm, deposited on a PET film (PA-2871©, BYK10 Gardner). Three measurements are carried out after 1 hour of drying at ambient temperature.

The sensitivity of the method for measuring haze is +/−0.3.

Protocol for Measuring the Viscosity

The viscosity of the formulas was measured using a Rheomat RM 200 rheometer from Lamy Rheology with spindle 4 (3 to 96 Pa·s) at a speed of 200 rpm. The measurements are expressed in Pa·s and determined at ambient temperature (25° C.), 24 hours after manufacture (t24 h) and after 2 months (t2 months), the value being taken at the end of 10 minutes of shearing (T10 min) (at T25° C./45° C.).

Evaluation of the Stability

A macroscopic evaluation of the formulas is carried out: colour, appearance and odour of the formula, as well as an evaluation by optical microscope (×20 in non-polarized and polarized white light). The viscosity and the pH of the formula is measured at multiple times/temperatures: after 24 hours at 25° C. and after 2 months at 25° C. and 45° C.

The sensitivity of the method for measuring viscosity is +/−2.4 Pa·s.

Protocol for the Sensory Study

The study is performed on a panel of 5 experienced persons: the evaluation is carried out of the back of the hand with an amount of 50 μl, and several sensory criteria are graded specifically, namely the criteria of fresh effect, dry effect, play time, tack and pilling effect (presence/appearance of pilling).

Example 1: Compositions 1 to 3

The compositions (1) according to the invention and (2) and (3) outside the invention, in the form of direct emulsions, were prepared on the basis of the compounds and contents detailed in Table 1 below. The contents are expressed as percentages by weight relative to the total weight of the composition.

TABLE 1

| Phase | Trade name/ Supplier | Compound or INCI name | Formula 1 according to the invention | Formula 2 outside the invention | Formula 3 outside the invention |
|---|---|---|---|---|---|
| A | | Glycol | 2.00 | 2.00 | 2.00 |
| A | | Water | qsp 100 | qsp 100 | qsp 100 |
| A | | Glycerine | 7.00 | 7.00 | 7.00 |
| A | | Preserving agents | 1.00 | 1.00 | 1.00 |
| A | | Chelating agent | 0.10 | 0.10 | 0.10 |
| A | | Poloxamer 338 | 0.30 | 0.30 | 0.30 |
| B | | Fatty acid | 1.80 | 1.80 | 1.80 |
| B | ARLACEL ® 165/ CRODA | Glyceryl Stearate (and) PEG-100 Stearate | 2.50 | 2.50 | 2.50 |
| B | | Guerbet alcohol | 2.00 | 2.00 | 2.00 |
| B | | Beeswax | — | — | 2.00 |
| B | | Fatty alcohol | 1.50 | 1.50 | 1.50 |
| B | | antioxidant | 0.07 | 0.07 | 0.07 |
| B | Intelimer ® IPA 13-1/ Evonik | Poly C10-30 Alkyl Acrylate | 2.00 | — | — |
| B | LIPEX SHEASOFT/ AARHUSKARLSHAMN | *BUTYROSPERMUM PARKII* (SHEA) BUTTER/*BUTYROSPERMUM PARKII* BUTTER | — | 5.00 | — |
| C | | Acrylates/C10-30 Alkyl Acrylate Crosspolymer | 0.20 | 0.20 | 0.20 |
| C | | Polyacrylamide (and) C13-14 Isoparaffin (and) Laureth-7 | 1.50 | 1.50 | 1.50 |
| C | | Xanthan Gum | 0.15 | 0.15 | 0.15 |
| C | | polysaccharide polymer | 2.00 | 2.00 | 2.00 |
| D | DOW CORNING ® VM-2270 AEROGEL FINE PARTICLES/ DOW CORNING (DOW CHEMICAL) | Silica Silylate | 0.50 | — | 0.50 |
| D | CELLULOBEADS ® USF/DAITO KASEI KOGYO | Cellulose | 1.50 | — | 1.50 |

Preparation of the Compositions

Each starting material of phase A was introduced into a beaker. This phase was then heated to 60° C. The starting materials of phase B, heated beforehand to 65-70° C., were then added. The mixture was emulsified on a high-speed emulsifier. Once the emulsion had been created, each of the starting materials of phases C to D were introduced at ambient temperature.

Three white creams are obtained.

Sensory Results

The sensory qualities of compositions (2) and (3) outside the invention and (1) according to the invention were tested. The criteria tested and assessments are reported in Table 2 below.

TABLE 2

| Qualities | Formula 1 according to the invention | Formula 2 outside the invention | Formula 3 outside the invention |
|---|---|---|---|
| Dry effect (+ very dry to +++ not dry) | ++ | +++ | ++ |
| Play time (+ long to +++ reduced) | +++ | ++ | ++ |
| Pilling effect (+ significant to +++ non existent) | +++ | +++ | +++ |
| Fresh effect (+ significant to +++ non-existent) | ++ | +++ | +++ |
| Tacky effect (+ significant to +++ little) | +++ | ++ | + |

Composition (1) according to the invention and composition (2) outside the invention have a good sensory aspect. In particular, they do not pill.

In particular, the sensory studies have shown that composition (1) according to the invention provides a dry effect, a moderate play time, a fresh and less tacky effect during and after application.

Composition (1) according to the invention displays a sensory aspect that is not degraded compared to composition (2) outside the invention, that is to say that composition (1) according to the invention retains (nearly) the same levels of sensory qualities as formula (2) outside the invention.

Haze Results

Haze measurements for evaluating the soft focus of compositions (1) according to the invention and compositions (2) and (3) outside the invention were carried out.

The results are detailed in Table 3 below.

TABLE 3

| Formulas | Formula 1 according to the invention | Formula 2 outside the invention | Formula 3 outside the invention |
|---|---|---|---|
| Haze (%) | 92.8 | 31.8 | 87.5 |

Composition (1) according to the invention therefore possesses an optimal level of soft-focus effect relative to the compositions outside the invention.

Stability Results

Compositions (2) and (3) outside the invention and (1) according to the invention were also tested in terms of stability, whether in terms of odour, colour, pH or viscosity, after 24 hours (t24 h) at 25° C. (Tamb) and over time after two months (t2 months) at 25° C. (Tamb) and at 45° C.

The results for viscosity and pH are described in detail in Table 4 below.

TABLE 4

| Viscosity values | Formula 1 according to the invention | Formula 2 outside the invention | Formula 3 outside the invention |
|---|---|---|---|
| Viscosity at t24 h and at $T_{amb}$, at 10 min | 6.4 Pa · s | 5.7 Pa · s | 6.9 Pa · s |
| pH at $t_{24\ H}$ and at $T_{amb}$ | 6.5 | 6.5 | 6.4 |
| Viscosity at $t_{2\ months}$ and at $T_{amb}$, at 10 min | 6.4 Pa · s | 7.8 Pa · s | 7.6 Pa · s |
| pH at $t_{2\ months}$ and at $T_{amb}$ | 6.5 | 6.4 | 6.4 |
| Viscosity at $t_{2\ months}$ and at $T_{45°\ C.}$, at 10 min | 7.3 Pa · s | 8.3 Pa · s | 6.9 Pa · s |
| pH at $t_{2\ months}$ and at $T_{45°\ C.}$ | 6.4 | 6.4 | 6.4 |

The three formulas prove to have satisfactory stability. Specifically, the measurements remain within the standard deviations for each measurement and/or are acceptable for the stability of cosmetic creams.

In conclusion, it appears that only formula (1) according to the invention according to the invention makes it possible to satisfy all expectations, namely good sensory qualities combined with a satisfactory soft-focus effect and stability.

The invention claimed is:

1. Composition comprising:

at least one particulate cellulosic compound;

at least hydrophobic silica aerogel particles; and at least one semicrystalline polymer containing at least one alkyl acrylate chain.

2. Composition according to claim 1, wherein the particulate cellulosic compound(s) are chosen from cellulosic compounds in the form of spheres, cellulosic compounds in the form of fibres, and mixtures thereof.

3. Composition according to claim 1, wherein the particulate cellulosic compound(s) are chosen from spherical cellulose beads and/or microcrystalline celluloses in the form of spheres.

4. Composition according to claim 1, wherein the content of particulate cellulosic compound(s) ranges from 0.1% to 10% by weight, relative to the total weight of the composition.

5. Composition according to claim 1, wherein the hydrophobic silica aerogel particles are particles of silylated silica aerogel (INCI name: silica silylate).

6. The composition as claimed in claim 1, wherein the content of hydrophobic silica aerogel particles ranges from 0.05% to 5% by weight, relative to the total weight of the composition.

7. Composition according to claim 1, wherein the semicrystalline polymer(s) containing at least one alkyl acrylate chain are chosen from the homopolymers obtained by polymerization of a monomer chosen from alkyl acrylates and alkyl methacrylates and from the copolymers obtained by copolymerization of a monomer chosen from alkyl acrylates and alkyl methacrylates with a hydrophilic monomer, and mixtures thereof.

8. Composition according to claim 1, wherein the semicrystalline polymer(s) containing at least one alkyl acrylate chain are chosen from a polystearyl acrylate, a polybehenyl acrylate, a behenyl acrylate/2-hydroxyethyl acrylate copolymer, a stearyl acrylate/2-hydroxyethyl acrylate copolymer, and one of the mixtures thereof.

9. Composition according to claim 1, wherein the content of semicrystalline polymer(s) containing at least one alkyl acrylate chain ranges from 0.5% to 3% by weight, relative to the total weight of the composition.

10. Composition according to claim 1, further comprising at least one non-volatile hydrocarbon-based oil.

11. Composition according to claim 1, comprising at least one gelling agent.

12. Composition according to claim 1, comprising at least one nonionic surfactant.

13. Cosmetic process for caring for keratin materials, comprising at least one step of applying to said keratin materials a composition as defined in claim 1.

* * * * *